US00PP19949P2

(12) United States Plant Patent
Head et al.

(10) Patent No.: US PP19,949 P2
(45) Date of Patent: Apr. 21, 2009

(54) ***ROSMARINUS* PLANT NAMED 'GOLD DUST'**

(50) Latin Name: *Rosmarinus officinalis*
Varietal Denomination: Gold Dust

(76) Inventors: Stephen Head, 10495 Reeves Road, Chilliwack, British Columbia (CA), V2P 6H4; Julie Head, 10495 Reeves Road, Chilliwack, British Columbia (CA), V2P 6H4

( * ) Notice: Subject to any disclaimer, the term of this patent is extended or adjusted under 35 U.S.C. 154(b) by 0 days.

(21) Appl. No.: 12/151,939

(22) Filed: May 12, 2008

(51) Int. Cl.
*A01H 5/00* (2006.01)

(52) U.S. Cl. ..... Plt./226
(58) Field of Classification Search ..... Plt./226
See application file for complete search history.

*Primary Examiner*—Annette H Para
*Assistant Examiner*—Georgia Helmer

(57) ABSTRACT

A new and distinct cultivar of *Rosmarinus* named 'GOLD DUST' that is characterized by dense upright habit, deep-blue flowers, and thick variegated leaves with dark-green centers and broad gold margins. In combination these traits set 'GOLD DUST' apart from all other existing varieties of *Rosmarinus* known to the inventor.

2 Drawing Sheets

Genus: *ROSMARINUS.*
Species: *officinalis*
Denomination: 'GOLD DUST'.

BACKGROUND OF THE INVENTION

The present invention relates to a new and distinct cultivar of rosemary grown as an ornamental for use in the landscape. The new cultivar from the family Lamiaceae is known botanically as *Rosmaririus officinalis* and will be referred to hereinafter by the cultivar name 'GOLD DUST'.

'GOLD DUST' was discovered, by the inventor, in 2004 as a naturally occurring branch sport of *Rosmarinus officinalis* 'Rex' (unpatented). The inventor selected 'GOLD DUST' in Chilliwack, British Columbia, based on the criterion of unique leaf variegation. 'GOLD DUST' was discovered in a commercially grown crop of 'Rex'. The parent is an individual *Rosmarinus officinalis* 'Rex'. The new *Rosmarinus* cultivar named 'GOLD DUST' is distinguishable from the parent by thick variegated leaves.

The closest comparison plant known to the inventor is *Rosmarinus* 'Golden Rain' (unpatented). The comparison plant exhibits lime green foliage with narrow green banding that fades during summer months. 'Golden Rain' is slow to root and exhibits low vigor. 'GOLD DUST' is distinguishable from the comparison plant by robust growth, strong stems, and bold year-round variegated foliage.

'GOLD DUST' exhibits dense upright habit, robust growth, deep-blue flowers, and thick variegated leaves with dark-green centers and broad gold margins. Dimensions are 38 cm. in height and 28 cm. in width in the first year. Dimensions at maturity are 102 cm. in height and 90 cm. in width. 'GOLD DUST' is hardy to USDA Zone 7. 'GOLD DUST' has not been observed to be more or less susceptible to the pests and diseases which are known to affect *Rosmarinus* plants in cultivation. Cultural needs include full sun, well-draining soil and minimal to moderate water.

First asexual propagation was conducted by the inventor in 2004 and took place in Chiliwack, British Columbia. The method of asexual propagation used was vegetative stem cuttings. Since that time under careful observation 'GOLD DUST' has been determined fixed, stable, and true to type in subsequent generations of asexual propagation.

SUMMARY OF THE INVENTION

The following traits have been repeatedly observed and represent the distinguishing characteristics of the new *Rosmarinus officinalis* cultivar named 'GOLD DUST'. These traits in combination distinguish 'GOLD DUST' from all other varieties of *Rosmarinus* known to the inventor. 'GOLD DUST' has not been tested under all possible conditions. Phenotypic differences may be observed with variations in environmental, climatic, and cultural conditions without however any variance in genotype.

1. 'GOLD DUST' exhibits dense upright habit.
2. 'GOLD DUST' exhibits robust vigor.
3. 'GOLD DUST' exhibits thick variegated leaves with dark-green centers and broad gold margins.
4. 'GOLD DUST' exhibits strongly aromatic foliage.
5. 'GOLD DUST' exhibits deep-blue flowers in spring.
6. 'GOLD DUST' reaches 102 cm. in height and 90 cm. in width at maturity.
7. 'GOLD DUST' is hardy to USDA Zone 7.

BRIEF DESCRIPTION OF THE DRAWINGS

The accompanying color drawings illustrate the overall appearance of the new *Rosmarinus* cultivar named 'GOLD DUST' showing colors as true as it is reasonably possible to obtain in color reproductions of this type. Color in the drawings may differ from color values cited in the detailed botanical description, which accurately describe the actual color of the new variety 'GOLD DUST'. Plants depicted in the drawings are 12-months-old in 1-litre containers grown out-of-doors.

Drawing labeled

Drawing labeled

Figure 1:
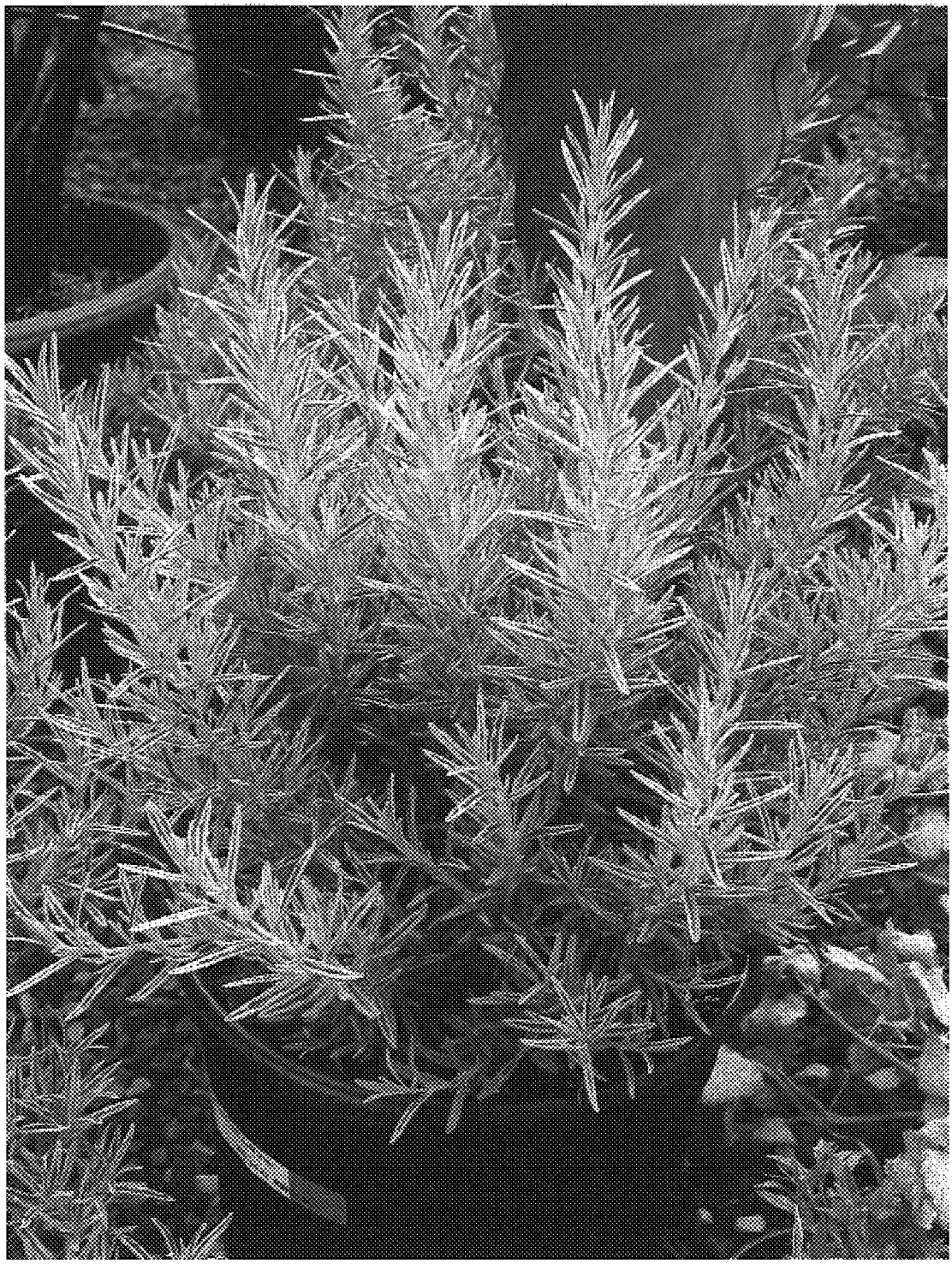
FIG. 1 depicts the entire plant 'GOLD DUST' from a side perspective.
Figure 2:
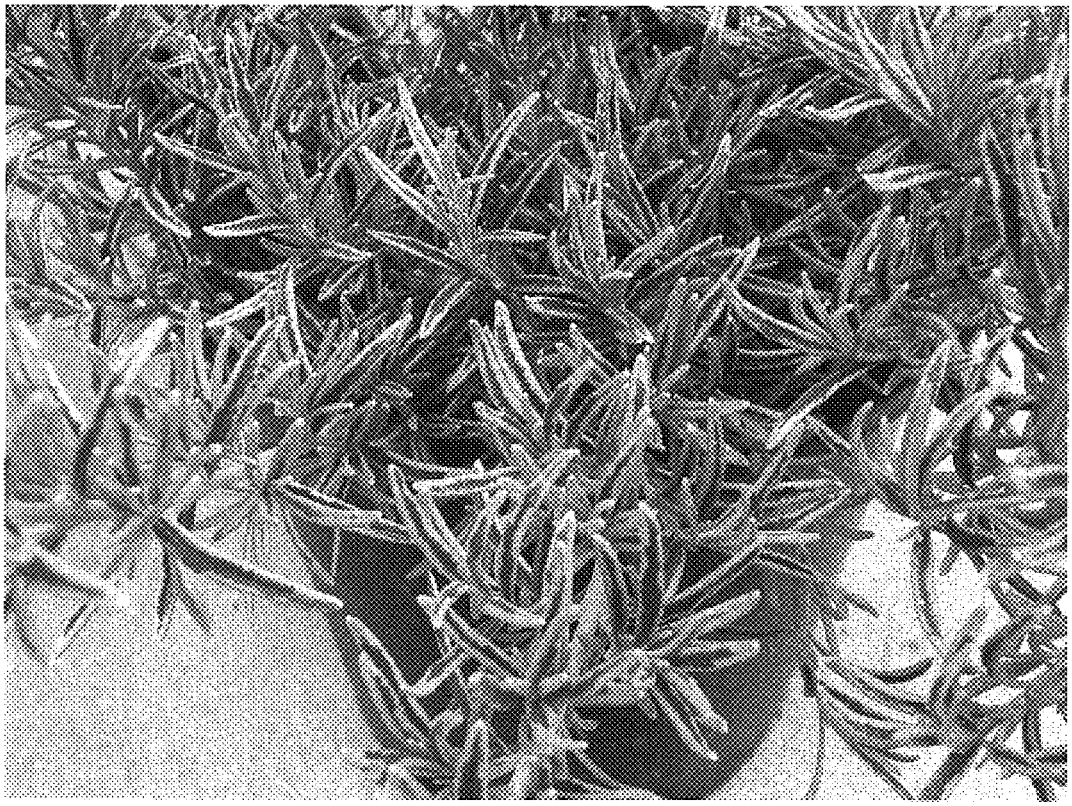
FIG. 2 depicts a close-up view of foliage highlighting the distinctive variegated foliage.

Drawings were made using conventional techniques and although flower and foliage color may appear different from the actual color due to light reflectance, they are as accurate as possible by conventional photography.

BOTANICAL DESCRIPTION OF THE PLANT

The following is a detailed botanical description of the new *Rosmarinus* cultivar named 'GOLD DUST'. Observations, measurements, values and comparisons were collected in Arroyo Grande, Calif. from 12-month-old plants in 1-litre containers that were grown out-of-doors. Color determinations are made in accordance with The Royal Horticultural Society Colour Chart of 2001 from London England, except where general color terms of ordinary dictionary significance are used. The growing requirements of the new variety are similar to the species.

Botanical classification: *Rosmarinus officinalis* 'GOLD DUST'.
Family: Labiatae.
Genus: *ROSMARINUS.*
Species: *officinalis.*
Denomination: 'GOLD DUST'.
Common name: Rosemary.
Parentage: *Rosmarinus officinalis* 'GOLD DUST' was discovered as a naturally occurring branch sport of the following:
*Parent.*—An individual *Rosmarinus officinalis* 'Rex' (unpatented).
Propagation method: Vegetative stem cuttings.
Rooting habit: Fine and fibrous.
Time to develop roots (range): Approximately 30–45 days are required to develop roots from an initial tip cutting.
Crop time: 6 months are required to achieve a finished 1-litre container from a rooted cutting.
Plant habit: Dense upright habit.
Commercial classification: Shrub.
Use: Ornamental for the landscape.
Vigor: Low to moderate.
Plant dimensions (first year): 38 cm. in height and 28 cm. in width.
Hardiness: USDA Zone 7.
Cultural requirements: Full sun, low to moderate water, and well-draining soil.
Pests and disease: None known to the inventor other than what typically affects rosemary.
Stem:
*Stem color.*—165A and 145A are both individually present.
*Stem shape.*—Sub-cylindrical.
*Stem width.*—4 mm.
*Stem length* (*average*).—20 cm.
*Internode length.*—0.75 cm.
*Stem fragrance.*—Aromatic scent when bruised.
*Stem surface.*—Glandular.
*Stem texture.*—Resinous.
Foliage:
*Type.*—Evergreen.
*Leaf arrangement.*—Whorled.
*Leaf division.*—Simple.
*Leaf shape.*—Linear.
*Leaf texture.*—Resinous.
*Leaf length* (*average*).—3 cm.
*Leaf width* (*average*).—0.30 cm.
*Leaf apex.*—Acute.
*Leaf base.*—Attenuate.
*Leaf quantity* (*average*).—175 leaves per stem.
*Leaf color* (*adaxial surface*).—147A and 10A.
*Leaf color* (*abaxial surface*).—147C and 10C.
*Leaf venation pattern.*—Reticulate.
*Vein color* (*adaxial surface*).—147A.
*Vein color* (*abaxial surface*).—Inconspicuous.
*Leaf margin.*—Entire and revolute.
*Leaf surface* (*adaxial*).—Coriaceous.
*Leaf surface* (*abaxial*).—Tomentose.
*Leaf attachment.*—Sessile.
*Leaf fragrance.*—Strongly aromatic.
Flower:
*Inflorescence type.*—Axillary cyme.
*Flower shape.*—Bilabiate.
*Flower color.*—93A.
*Bud dimensions.*—3 mm. in length and 2.50 mm. in width.
*Bud apex.*—Obtuse.
*Bud shape.*—Ovoid.
*Bud color.*—N186A.
*Bud surface.*—Tomentose.
*Corolla depth.*—1.25 cm.
*Corolla diameter.*—1.75 cm.
*Corolla tube depth.*—3 mm.
*Corolla.*—2-lipped and strongly exserted.
*Upper lip.*—2-lobed.
*Upper lobe apices* (*range*).—Rounded to obovate.
*Upper lip shape.*—Concave.
*Upper lip margin.*—Entire.
*Lower lip.*—3-lobed.
*Lower lobe apices.*—Rounded.
*Middle lobe shape.*—Spoon-shaped.
*Lower lip margin.*—Entire.
*Upper and lower lip dimensions* (*range*).—4–6 mm. in length and 3–8 mm. in width.
*Upper and lower lip color* (*adaxial and abaxial surfaces*).—93A.
*Upper and lower lip surfaces* (*adaxial and abaxial surfaces*).—Glabrous.
*Lips fused or unfused.*—Lips are basally fused.
*Flowering season.*—Spring.
*Aspect.*—Facing outward and upward.
*Flower quantity* (*average*).—9 per inflorescence.
*Peduncle dimensions.*—3 mm. in length and 1 mm. in width.
*Peduncle shape.*—Sub-cylindrical.
*Peduncle surface.*—Lanate.
*Peduncle color.*—147C.
*Calyx shape.*—Campanulate.
*Calyx color.*—N187B.
*Calyx surface.*—Tomentose.
*Calyx dimensions.*—5 mm. in height and 3 mm. in width.
*Number of sepals.*—3 in number.
*Fused or unfused.*—Fused.
*Seal apex.*—Broadly acute.
*Sepal margins.*—Entire.
*Sepal color* (*adaxial and abaxial surfaces*).—N187B.
*Flower fragrance.*—None observed.
Reproductive organs:
*Stamen.*—2 parallel and strongly exserted.
*Stamen length.*—1 cm.
*Stamen color.*—98D.
*Anther dimensions.*—1.50 mm. in length and 1.50 mm. in width.
*Anther shape.*—Disc-shaped.

*Anther color.*—156D.
*Pollen.*—None observed.
*Pistil.*—One in number.
*Pistil length.*—1 cm.
*Pistil color.*—98D.
*Stigma color.*—98D.
*Stigma length.*—1.50 mm.
*Style.*—Unbranched.
*Ovary position.*—Superior.
*Ovary shape.*—Globular.
*Ovary dimensions.*—1.50 mm. in height and 1.50 mm. in diameter.
*Ovary color.*—N144A.

Seed: No seed observed to date.

What is claimed is:

1. A new and distinct variety of *Rosmarinus* plant named 'GOLD DUST' as illustrated and described herein.

* * * * *